ID [19] United States Patent
Undheim et al.

[11] Patent Number: 5,731,289
[45] Date of Patent: Mar. 24, 1998

US005731289A

[54] DOUBLE-CHAIN HEMOREGULATORY PEPTIDES

[75] Inventors: Kjell Undheim, Sandvika; Meinolf Lange; Jessie Sandosham, both of Oslo, all of Norway

[73] Assignee: Nycomed Imaging AS, Oslo, Norway

[21] Appl. No.: 648,016

[22] PCT Filed: Nov. 30, 1994

[86] PCT No.: PCT/GB94/02621

§ 371 Date: Aug. 8, 1996

§ 102(e) Date: Aug. 8, 1996

[87] PCT Pub. No.: WO95/15336

PCT Pub. Date: Jun. 8, 1995

[30] Foreign Application Priority Data

Dec. 1, 1993 [GB] United Kingdom ............... 9324691

[51] Int. Cl.$^6$ .................. A61K 38/04; A61K 38/08; C07K 7/00

[52] U.S. Cl. .................. 514/14; 514/15; 514/16; 514/17; 514/18; 530/327; 530/328; 530/329; 530/330; 530/333

[58] Field of Search .............. 514/14–18; 530/327–330, 530/333

[56] References Cited

U.S. PATENT DOCUMENTS 4,528,190  7/1985  Vale, Jr. et al. .................. 514/12

FOREIGN PATENT DOCUMENTS

| 0 408 371 | 1/1991 | European Pat. Off. . |
| 88/03535 | 5/1988 | WIPO . |
| 93/24522 | 12/1993 | WIPO . |
| 93/24523 | 12/1993 | WIPO . |

OTHER PUBLICATIONS

Spatola, "Chemistry and Biochemistry of Amino Acids, Peptides & Proteins" vol. 7 (Marcel Dekker 1983) pp. 284–295.

*Primary Examiner*—Cecilia J. Tsang
*Assistant Examiner*—Bennett Celsa
*Attorney, Agent, or Firm*—Bacon & Thomas

[57] ABSTRACT

The present invention relates to peptide compounds comprising two single-chain hemoregulatory, for example haemopoiesis-inhibiting, peptides linked by a bridging group terminally attached to the Cα atoms of non-terminal amino acids wherein at least one of the Cα atoms is independently substituted by an alkyl group. The bridged dipeptide compounds have a stimulating activity on cell division, especially in myelopoietic and bone marrow cells.

9 Claims, No Drawings

DOUBLE-CHAIN HEMOREGULATORY PEPTIDES

This application is a 371 of PCT/GB94/02621 filed Nov. 30, 1994.

1. FIELD OF THE INVENTION

The present invention relates to the use of peptides having a stimulating effect on cell proliferation, and to novel peptides having specific and/or general cell stimulating effects.

2. DESCRIPTION OF RELATED ART

The mammalian body contains cells having enormously diverse structures and functions, and the mechanisms of differentiation and development have been the focus of much study. It is known that for systems of cells having a continuous turnover the mechanism commonly involves a reservoir of pluripotent stem cells which divide and constantly supply new cells to the system. While initially homogeneous the stem cells supplied from the "reservoir" soon become committed to one or other morphology and subsequently develop into the required functional cells:

Examples of such stem cell systems are the haemopoietic system in bone marrow and the epithelial and epidermal systems.

The manipulation or control of stem cell division is of great potential therapeutically and much research continues to be devoted to elucidating the mechanisms involved and the chemical messengers responsible. To date several biomolecules have been identified as possessing a role in cell production and differentiation either by the stimulation or inhibition of a step within the process. Myelopoiesis has been particularly well studied in this regard and molecules involved in its control include: colony-stimulating factors (CSF) such as granulocyte colony-stimulating factor (G-CSF), macrophage colony-stimulating factor (M-CSF), granulocyte-macrophage colony-stimulating factor (GM-CSF), multi-lineage colony-stimulating factor (multi-CSF; IL-3) [see Metcalf, Science 229: 16 (1985)], interleukin 11 (IL-11) [see Paul et al Proc Natl Acad Sci USA 87: 7521 (1990)], Lactoferrin [see Broxmeyer et al Blood Cells 11: 429 (1986)], prostoglandins [see Pelus et al J. Immuno 140: 479 (1988)], acidic (H-subunit) ferritin [see Broxmeyer et al Blood 68: 1257 (1986)], interferons ($\alpha$, $\beta$ and) [see Pelus et al supra. and Broxmeyer et al J. Immunol 131: 1300 (1983)], tumour necosis factors ($\alpha$ and $\beta$) [see Broxmeyer et al J Immunol 136: 4487 (1986)], transforming growth factor-$\beta$ [see Ottman et al J Immunol 140: 2661 (1988)], and activin and inhibin [see Broxmeyer et al Proc Natl Acad Sci USA 86: 779 (1989)].

It has also been found that the haemoregulatory pentapeptide (pEEDCK) inhibits the proliferation of myelopoietic cells selectively [see Paukovits et al Z. Naturforsch 37: 1297 (1982)] and other peptides corresponding to a narrow general formula were discovered to exert a similar inhibitory effect in hemopoiesis [see EP-A-112656 and WO90/02753]. Oxidation of the peptide monomers resulted in dimeric molecules linked by a cysteine bridge and these dimeric molecules were found to stimulate myelopoiesis [see Laerum et al. Exp. Hematol 16: 274 (1988)]. The (pEEDCK)$_2$ dimer and other similar compounds are disclosed in WO-A-88/03535. Further dimeric peptide compounds are disclosed in EP-A-408371 in which the disulphide bond has been replaced by a carbon or carbon/sulphur bridge linking the selected peptide chains. The bridge is thus relatively stable to hydrolysis but is itself inert and incapable of participating in receptor-dimer interactions.

Novel single-chain peptide compounds capable of inhibiting cell proliferation are also described and claimed in our PCT application filed under No. PCT/GB93/01172 and further dimeric compounds having a stimulatory effect on cell proliferation are disclosed in our PCT applications filed as PCT/GB93/01170 and PCT/GB93/01171.

Whilst we do not wish to be bound by theoretical considerations, it is presently believed that such peptide compounds interact with stromal cells in vivo and that the stromal cells are responsible for stimulating or inhibiting cellular division via other soluble factors. The dimers are thus believed to induce or promote stromatic production of stimulatory cellular regulatory factor(s) whilst the monomeric peptides may either inhibit that process or cause the production of factors which prevent or hinder cell division. Thus, according to current thinking, the stromal cells may act to amplify the stimulatory or inhibitory effects of the dimeric and monomeric peptides respectively.

There is a continuing need for dimeric peptide compounds capable of stimulating cell proliferation to a useful level in vivo. In this regard it should be noted that different degrees of stimulation may be more appropriate to certain clinical situations than to others and, in particular, selective stimulation of individual cell types is important.

3. SUMMARY OF THE INVENTION

The present invention relates to certain novel peptides having a stimulatory effect on cell proliferation and having conformational preferences which will maximise the interaction of the pharmacophoric regions of the peptides with the receptors where the peptides are to exert their biological action. In particular, the invention relates to dimeric peptides comprising two peptide chains linked by a bridge between $\alpha$-carbon atoms of an amino acid in each chain, in which conformational constraints are achieved by the presence of an alkyl group on at least one of said $\alpha$-carbon atoms. Alkylation at the $\alpha$-carbon also serves to greatly reduce the ease of enzymatic cleavage of the peptide bonds in the vicinity of the bridge amino acid.

4. DESCRIPTION OF THE PREFERRED EMBODIMENTS

Thus, viewed from one aspect the present invention provides a peptide compound comprising two single-chain hemoregulatory, for example haemopoiesis-inhibiting, peptides linked by a bridging group terminally attached to the C$\alpha$ atoms of non-terminal amino acids wherein at least one of said C$\alpha$ atoms is independently substituted by an alkyl group.

Preferred peptide compounds according to the present invention are those of formula I:

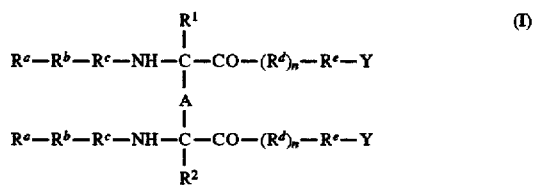

(wherein R$^1$ and R$^2$ independently represent hydrogen atoms or C$_{1-4}$-alkyl groups with the proviso that R$^1$ and R$^2$ may not simultaneously represent hydrogen atoms;

A represents a carbon-carbon bond or an optionally substituted, saturated or unsaturated C$_{1-8}$-alkylene or aralkylene group which may be interrupted by one or more O or S atoms or —S—S— groups;

each R$^a$ independently represents pyroglutamic acid (pGlu), pyridine-2-carboxylic acid (Pic) or a 3-amino or 3-hydroxy derivative thereof, anthranilic acid, pyridine-3-carboxylic acid (Nic), pyrazine-2-carboxylic acid, pyrrole-2-carboxylic acid, proline or pipecolic acid;

each $R^b$ independently represents serine (Ser), glutamic acid (Glu), aspartic acid (Asp), threonine (Thr) or allothreonine (aThr);

each $R^c$ independently represents aspartic acid (Asp) or glutamic acid (Glu);

each $R^d$ independently represents glycine (Gly) or alanine (Ala);

each $R^e$ independently represents Lysine (Lys), ornithine (Orn) or arginine (Arg);

each Y independently represents a hydroxy or amino group, or an amine of an amino acid; and n represents 0 or 1).

All the said amino acid residues may be in either the D or the L form. The L form of the amino acids is, however, preferred.

Each Cα atom at the bridging point of each peptide chain may have the stereochemistry (R,R), (S,S) or (R,S).

Particularly preferred peptide compounds according to the invention include those of formula I wherein A represents a carbon-carbon bond, a $C_{1-6}$-alkylene group, cis or trans —$CH_2$—CH=CH—$CH_2$—, $CH_2$—C≡C—$CH_2$—, —$(CH_2)_p$—Z—$(CH_2)_q$ wherein Z=O, S or $S_2$ and p and q independently represent 1 or 2, or —$(CH_2)_r$—$C_6H_4$—$(CH_2)_s$, wherein r and s independently represent 0 or 1.

More particularly preferred peptide compounds according to the invention include those of formula I wherein A contains an even number of atom, for example a $C_2$— or $C_4$— alkylene group.

One especially preferred peptide compound of formula I is induce alternating peaks of high and low activity in the bone marrow cells, thus augmenting the natural circadian rhythm of haemopoiesis. In this way, cytostatic therapy can be given at periods of low bone marrow activity, thus reducing the risk of bone marrow damage, while regeneration will be promoted by the succeeding peak of activity.

In general, in order to exert a stimulatory effect, the peptides of the invention may be administered to human patients orally or by injection in the dose range 0.001–100 mg, for example 1–5 mg, per 70 kg body weight per day. If administered intravenously or subcutaneously, the dose may be in the range 1–10 mg per 70 kg body weight per day, for example about 6 mg, for up to ten days. Nasal, topical (transdermal) or rectal administration is, of course, also feasible. In principle it is desirable to produce a concentration of the peptide of about $10^{-13}$M to $10^{-5}$M in the extracellular fluid of the patient.

According to a further feature of the present invention there are provided pharmaceutical compositions comprising as active ingredient one or more compounds of formula (I) as hereinbefore defined or physiologically compatible salts thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays,

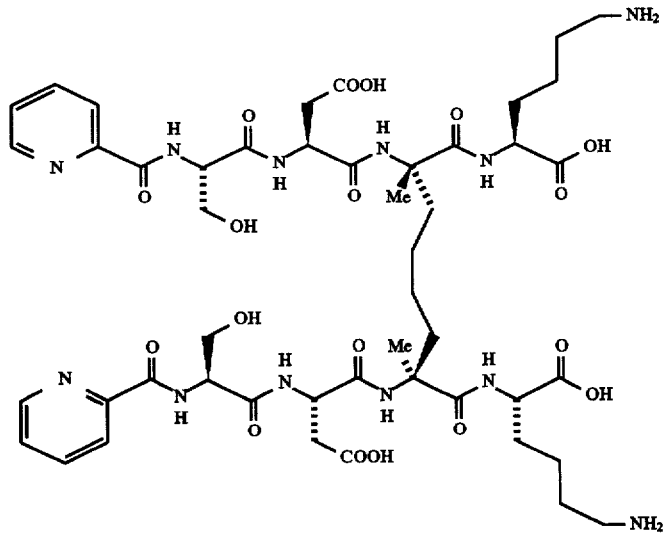

The invention is of particular application in stimulating myelopoiesis in patients suffering from reduced myelopoietic activity, including bone marrow damage, agranulocytosis and aplastic anaemia. This includes treatment of patients having depressed bone marrow function due to immunosuppressive treatment to suppress tissue reactions, e.g. in bone marrow transplant surgery.

The compounds may also be used to promote more rapid regeneration of bone marrow after cytostatic chemotherapy and radiation therapy for neoplastic and viral diseases.

In addition, the new compounds may be of particular value where patients have serious infections due to lack of immune response following bone marrow failure.

Another clinical application will be in combination with the corresponding monomers or related myelopoiesis inhibitors as disclosed in EP-A-112656 or WO-A-90/02753 to solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

According to a still further feature of the present invention there is provided a method of stimulation of cell division, especially myelopoiesis which comprises administering an effective amount of a pharmaceutical composition as hereinbefore defined to a subject.

A further major use of the new peptides, however, is in the production of material for immunological assay techniques. The peptide may then be covalently attached to a suitable high molecular carrier such as albumin, polylysine or polyproline in order to be injected into antibody-producing animals (e.g. rabbits, guinea pigs or goats). In vitro immunisation techniques may also be used. High specificity antisera are obtained by use of well known absorption techniques, using the high molecular carrier. By introducing radioactivity ($^3$H, $^{125}$I, $^{14}$C, $^{35}$S) into the peptide molecule, a radioimmuno assay can be designed and used for determining the peptide in the different biological fluids such as serum (plasma), urine and cerebrospinal fluid.

The peptides of the invention may be synthesized in any convenient way. In solid phase synthesis success hinges on the ability to drive all the reactions taking place on the solid phase to completion. Conventional peptide synthesis incorporates several methods whereby completeness of acylation and deprotection can be controlled. These methods typically utilise large excesses of coupling and deprotecting reagents. They also include a battery of methods designed to monitor solid phase reactions based on staining of resin beads (ninhydrin, 2,4,6-trinitrobenzenesulfonic acid etc.).

The conventional peptide synthesis monitoring techniques cannot however be applied to the attachment of the diamino diacid to the immobilised amino acid or peptide because of the need for an excess of the amino acid or peptide groups in the solid phase. Firstly, it is essential to couple both acid functions of the bridge diamino diacid to a preloaded resin with lysine or any other C-terminal amino acid. This requires the use of fewer equivalents of amino acid compared to resin functionality. The acylation therefore cannot be monitored using standard techniques due to the large excess of unreacted amino acid attached to the resin. Secondly, analysis of resin samples containing Fmoc-deprotected α-alkyl amino acids is hindered by the fact that standard techniques cannot be applied. The ninhydrin reaction, i.e. formation of Ruhemanns purple, cannot be used and complete deprotection and acylation with for instance FmocAsp(OtBu)OH cannot be monitored. Due to the low availability and high cost of the α-alkyl diamino diacids, some form of monitoring is vital during these crucial coupling cycles.

The problems detailed above have been overcome by accurately calculating coupling efficiency using a UV technique. The Fmoc/piperidine mixture formed during the deprotection step was used to give an accurate measure of coupling efficiency. Resin samples were removed from the reaction vessel at various stages and analysed. The absorbance values, when applied to a standard curve, give a numerical value of amino acid incorporation.

Schöllkopf et al have described the preparation of a variety of amino acids by the metallation and subsequent alkylation of bis-lactim ethers (see, for example, Tetrahedron 39: 2085 (1983) and Topics Curr. Chem 109: 65 (1983)). An adaptation of this method, replacing the alkylation step by reaction with a bifunctional bridging reagent which links two bis-lactim ether groups, has proved particularly useful for the preparation of the α-alkylated bridged amino acids of the present invention. In particular, the bis-lactim ether derived from a cyclised alanine-alanine dipeptide yields the corresponding. 2,2-disubstituted bis-lactim ether following metallation and alkylation, which on hydrolysis furnishes the α-methyl-α-amino acid (see, for example, Liebigs Ann. Chem. 696 (1981)). This can be adapted to prepare α-methyl diamino diacids. Similarly, the bis-lactim ether derived from an (L)- or (D)-cyclised leucine-leucine dipeptide can be converted into an α-isobutyl-α-amino acid (see, for example, Synthesis 271 (1984)). This can be adapted to prepare α-isobutyl diamino diacids.

In general, for the larger α-alkyl derivatives, dimerisation of the corresponding α-amino acid and conversion into a bis-lactim ether produces a convenient starting material for the subsequent bridging alkylation reaction; for the smaller alkyl groups, for example methyl, initial alkylation of the commonly used bis-lactim ether derived from a valine-glycine dipeptide may be followed by a second alkylation, which will take place on the same bis-lactim carbon i.e. in the 2-position. Subsequent hydrolysis yields the corresponding α-alkyl-α-amino acid.

Alternatively, α-methylated amino acids are conveniently available from the bis-lactim ether derived from (L)- or (D)-valine and alanine. Racemic alanine can be used since the stereochemistry at the alanine derived α-carbon is lost following metallation. The new group on this carbon enters trans to the isopropyl group such that the newly formed amino acid will have the (L)-configuration if (D)-valine is used and vice versa.

The method of Schöllkopf et al may be adapted for the synthesis of the α-alkylated bridged amino acids of the present invention as illustrated in the following general reaction scheme wherein $R^1$, $R^2$ and A are as defined above; $R^3$ and $R^4$ are either the same as $R^1$ and $R^2$ respectively or are alkyl groups providing steric protection of the α-carbon atoms to which they are attached; and $R^5$, $R^6$, $R^7$ and $R^8$ independently represent $C_{1-6}$ alkyl groups e.g. methyl or $C_{1-8}$ aralkyl groups such as benzyl.

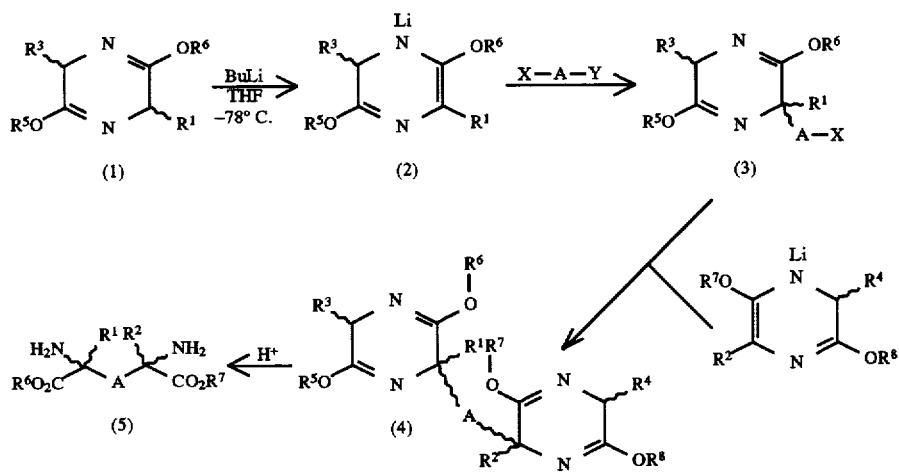

(1) (2) (3)

(5) (4)

The loss of stereochemistry at the 2-position in the bis-lactim ether (1) on metallation can be seen from the above reaction scheme. On alkylation with what is to become bridge A the new substituent enters trans to the group $R^3$ (usually isopropyl) in the 6-position (3). Using an equivalent amount for half alkylation the reaction can be stopped at this stage and the product (3) isolated. The product from the first alkylation can be further reacted with another bis-lactim ether where the substituent $R^2$ in the 2-position is the same or different from $R^1$ giving a symmetrically or unsymmetrically dialkylated product (4), respectively. Hydrolysis then furnishes the corresponding symmetrical or unsymmetrical bridged amino acid (5). In both alkylations the bridge grouping enters trans to the group $R^3$ or $R^4$. (L)-Valine ($R^3$=isopropyl) in both the bis-lactim ethers therefore gives rise to the (R,R)-α,α'-diamino diacids, whereas the (D)-valine bis-lactim ethers yield (S,S)-α,α'-diamino diacids. When the valine in one of the bis-lactim ethers has the (L)-configuration, and in the other has the (D)-configuration, the corresponding (R,S)-diamino diacid is formed, which is the meso-form when $R^1$ is the same as $R^2$.

When the alkylating agent has two vicinal bromine atoms such as in 1,2-dibromoethane, bromination of the bis-lactim ether is the faster reaction. The initially formed product couples with another bis-lactim ether. The dimer on hydrolysis forms 2,3-diamino-2,3-dimethylbutanedioic acid (succinic acid) i.e. A is a carbon-carbon bond. The preparation of ethylene bridged compounds may therefore be achieved by using 1-bromo-2-chloroethane for alkylation. The intermediate 2-(2-chloroethyl) derivative is isolated, and in order to facilitate the second alkylation the chlorine substituent is preferably exchanged in a prior reaction with bromide or iodide ions.

An alternative method for the preparation of the peptide compounds of the present invention can be illustrated by the following general reaction scheme in which $R^1$, $R^2$, $R^3$, $R^4$, $R^5$, $R^6$, $R^7$, $R^8$, and A are as hereinbefore defined.

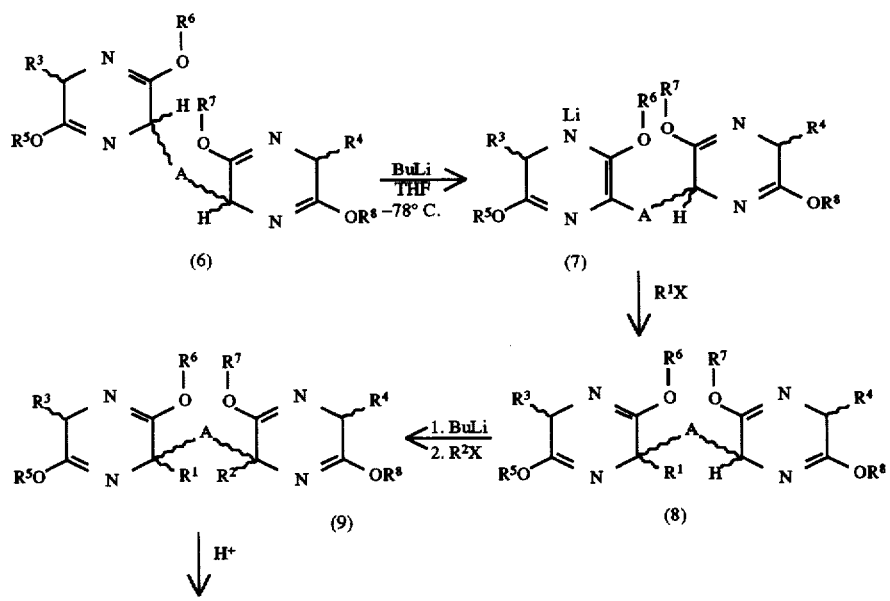

(6) (7)

(9) (8)

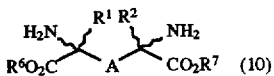 (10)

The dipeptide (6) used as starting material in the above reaction scheme may be prepared as described in our earlier co-pending cases, PCT/GB93/01170 and PCT/GB93/01171.

Again, on metallation at the 2-position (7) the stereochemistry at the bridge-attached carbon is lost. In the example shown, the configuration at this carbon is inverted on alkylation (9). The reaction can be stopped at this stage, and the product (9) hydrolysed to form the corresponding diamino diacid. Alternatively, a second alkylation with configurational inversion may be followed by hydrolysis to furnish the corresponding diamino diacid (10).

The bis-lactim dipeptide ethers (4), (7), (8) and (9) and bridged α,α'-diamino acids (5) and (10) produced by the above described techniques form a further aspect of the present invention.

The diamino diacids are preferably converted into N-Fmoc derivatives before the coupling reactions according to the solid phase protocol. The diamino diacid diester in dioxane:water and sodium bicarbonate may be acylated with Fmoc-Cl as reagent and the ester groups in the Fmoc-protected product may then be hydrolysed to the diacid by heating in 6N HCl. Alternatively, the diamino diacid may be N-acylated by Fmoc-Cl in dioxane:water as sodium salt. In yet another approach the diamino diacid may initially be persilylated by heating the diamino diacid in HMDS with some TMS-Cl added. The persilylated product is soluble in dichloromethane and may be acylated by adding Fmoc-Cl and heating the resultant solution.

Thus, viewed from a further aspect the present invention provides a process for producing a peptide compound, said process comprising:

(a) hydrolysing a compound of the formula

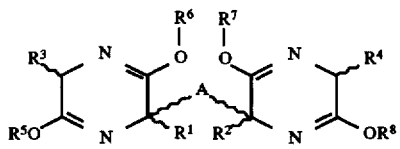

wherein A, $R^1$, $R^2$, $R^3$, $R^4$, $R^5$, $R^6$, $R^7$ and $R^8$ have the above meanings to form a diamino diacid derivative of the formula

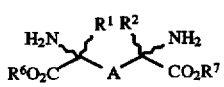

(b) reacting said diamino diacid derivative with successive amino acid derivatives to build up a protected derivative of the bridged peptide of formula I and
(c) deprotecting any protected groups present.

In general, deprotection will always be required and according to a further aspect of the invention we provide a process for the production of a compound of formula I as defined above wherein a protected derivative thereof is subjected to deprotection.

Once the bridged dipeptide has been formed, then the remaining amino acids in the peptide chain can be introduced using conventional techniques.

In building up the peptide chains, one can in principle start either at the C-terminal or the N-terminal.

Thus, one can start at the C-terminal by reaction of the diamino diacid with, for example, a suitably protected derivative of lysine. The lysine derivative will have a free α-amino group while the diamino diacid will have either a free or activated carboxyl group and a protected amino group. After coupling, the intermediate may be purified for example by chromatography, and then selectively N-deprotected to permit addition of a further N-protected and free or activated amino acid residue. This procedure is continued until the required amino acid sequence is completed.

Carboxylic acid activating substituents which may, for example, be employed include symmetrical or mixed anhydrides, or activated esters such as for example p-nitrophenyl ester, 2,4,5,trichlorophenylester, N-hydroxybenzotriazole ester (OBt), N-hydroxysuccinimidylester (OSu) or pentafluorophenylester (OPFP).

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline (EEDQ).

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start the C-terminal, for example by coupling N-protected lysine to the support.

A number of suitable solid phase techniques are described by Eric Atherton, Christopher J. Logan, and Robert C. Sheppard, J. Chem. Soc. Perkin I, 538–46 (1981); James P. Tam, Foe S. Tjoeng, and R. B. Merrifield J. Am. Chem. Soc. 102, 6117–27 (1980); James P. Tam, Richard D. Dimarchi and R. B. Merrifield Int. J. Peptide Protein Res 16 412–25 (1980); Manfred Mutter and Dieter Bellof, Helvetica Chimica Acta 67 2009–16 (1984).

It is also possible for the coupling reactions to be performed in solution.

A wide choice of protecting groups for amino acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag Stuttgart, NY, 1983; The Peptides, Analysis, synthesis, biology 1–7, Ed: Erhard Gross, Johannes Meienhofer, Academic Press, NY, San Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (Z-), t-butoxycarbonyl (Boc-), 4-methoxy-2,3,6-trimethylbenzenesulphonyl (Mtr-), and 9-fluorenylmethoxycarbonyl (Fmoc-). It will be appreciated that when the peptide is built up from the C-terminal end, an amine protecting group will be present on the α-amino group of each new residue added and will need to be removed selectively prior to the next coupling step. For solid phase systems one particularly useful group for such temporary amine protection is the Fmoc group which can be removed selectively by treatment with piperidine in an organic solvent. For synthesis in solution, Boc- is a preferred protecting group, which can be introduced and removed in a conventional manner.

Carboxyl protecting groups which may, for example be employed include readily cleaved ester groups such as benzyl (—OBZl), p-nitrobenzyl (—ONB), or t-butyl (-tOBu) as well as the coupling on solid supports, for example methyl groups linked to polystyrene.

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting groups prior to the next coupling step.

Amine protecting groups such as Boc and carboxyl protecting groups such as tOBu may be removed simultaneously by acid treatment, for example with trifluoro acetic acid.

The following Examples are given by way of illustration only.

The following abbreviations are used in the following Examples:

| | |
|---|---|
| Asp = | aspartic acid |
| But = | tert. butyl |
| Ser = | serine |
| Glu = | glutamic acid |
| pGlu = | pyroglutamic acid |
| PyBOP = | (benzotriazolyoxy-tris[pyrrolidino]-phosphonium hexafluorophosphate |
| HOBt = | 1-hydroxybenzotriazole |
| NMM = | 4-methylmorpholine |
| DMF = | dimethylformamide |
| DMAP = | N,N-dimethylaminopyridine |
| Pic = | 2-picolinic acid |
| Boc = | tert. butyloxycarbonyl |
| DIC = | diisopropylcarbodiimide |
| DCM = | dichloromethane |
| TFA = | trifluoroacetic acid |
| HPLC = | high performance liquid chromatography |

For consistency, throughout the following Examples, the isopropyl group has been numbered as being in the 5-position.

All $^1$H NMR were recorded at 300 MHz, and all $^{13}$C NMR at 75 MHz.

General procedure for alkylation of 2,5-dihydro-3,6-dimethoxy-5-isopropyl-2-methyl-pyrazine A solution of n-butyllithium in hexane (1.60M solution; 3.44 ml, 5.5 mmol) was injected into a solution of (5R, 2R,S)-2,5-dihydro-3,6-dimethoxy-5-isopropyl-2-methylpyrazine(5 mmol) and DMEU (10 mol) in THF (50 ml), and the mixture stirred for 15–20 min to complete the formation of the aza enolate. Then a solution of the alkyl halide (2.75 mmol) in THF (10 ml) was added and the mixture stirred at −78° C. The reaction time was monitored by TLC (vide infra). The reaction was quenched by addition of phosphate buffer, the mixture allowed to warm up to room temperature, the solvent evaporated at reduced pressure and the residue shaken with water (30 ml) and diethyl ether (50 ml). The layers were separated and the water layer extracted twice with ether (2×25 ml). The combined ether solution was dried (MgSO$_4$) and the ether distilled off. The crude product was purified by bulb to bulb distillation or flash-chromatography. The diastereomeric ratio of the crude product was determined by capillary GLC.

EXAMPLE 1

Dialkylation without isolation of monoalkylated intermediate 1,3-Bis-[(2S,5R)-2,5-dihydro-3,6-dimethoxy-5-isopropyl-2-methyl-2-pyrazinyl]propane The general procedure outlined above was used. The reagents used were (5R, 2R,S) -2,5-dihydro-3,6-dimethoxy-5-isopropyl-2-methylpyrazine (3.1 g, 15.64 mmol), THF (170 ml), DMEU (3.57 g, 31.28 mmol), n-butyllithium (1.6M; 10.75 ml, 17.20 mmol) and 1,3-dibromopropane (1.58 g, 7.82 mmol) in THF (25 ml). Stirring was continued for 17 h at −78° C. The excess of dibromopropane was removed from the crude mixture by evaporation at 40° C./0.01 torr. The product was purified by flash-chromatography on silica gel 60 using hexane; diethyl ether (15:1).

Yield 2.56 g (75%). mp. 65.2° C. (nitromethane). Capillary GLC: d.e. 88%. IR (KBr): 1690 cm$^{-1}$ (C=N) $^1$H NMR (CDCl$_3$): δ 0.66 and 1.05 (2 d; J 7.7 Hz; 6H; —CH(C$\underline{H}_3$)$_2$), 0.71–0.82 (m;1H;—CH$_2$—C$\underline{H}_2$—CH$_2$—), 1.27(s;3H; 2-CH$_3$), 1.32–1.81 (m;2H;—C$\underline{H}_2$—CH$_2$—CH$_2$—), 2.20 (dsp;J1 7.7 Hz, J2 4.0 Hz; 1H,—C$\underline{H}$(CH$_3$)$_2$), 3.61 (s; 6H; —OC$\underline{H}_3$), 3.87 (d; J 4.0 Hz; 1H; 5-$\underline{H}$).

1,4-Bis[(2S, 5R)-2,5-dihydro-3,6-dimethoxy-5-isopropyl-2-methyl-2-pyrazinyl]butane The general procedure outlined above was used. The reagents used were (5R, 2R,S)-2,5-dihydro-3,6-dimethoxy-5-isopropyl-2-methylpyrazine (4.0 g, 20.18 mmol), THF (190 ml), DMEU (4.61 g, 40.36 mmol), n-butyllithium (1.6M; 13.87 ml, 22.20 mmol) and 1,4-dibromobutane (2.18 g, 10.08 mmol) in THF (40 ml). Stirring was continued for 18 h at −78° C. The excess of dibromobutane was removed from the crude mixture by evaporation at 40° C./0.01 torr. The product was purified by flash-chromatography on silica gel 60 using hexane;diethyl ether (15:1).

Yield 3.72 g (82%). mp. 57° C. (nitromethane) Capillary GLC; d.e. 88.4% IR (KBr): 1690 cm$^{-1}$ (C=N). $^1$H NMR (CDCl$_3$): δ 0.66 and 1.04(2 d; J 6.9 Hz; 6H; —CH(C$\underline{H}_3$)$_2$), 0.89–1.07(m;4H;—CH$_2$—C$\underline{H}_2$—C$\underline{H}_2$—CH$_2$—),1.29(s;3H; 2-CH$_3$), 1.38–1.90 (m; 4H; —C$\underline{H}_2$—CH$_2$—CH$_2$—C$\underline{H}_2$—), 2.25(dsp;J1 6.9 Hz, J2 3.4 Hz; 1H, —C$\underline{H}$(CH$_3$)$_2$), 3.64(s; 6H; —OC$\underline{H}_3$), 3.91 (d;J 3.4 Hz; 1H;5-$\underline{H}$). $^{13}$C NMR (CDCl$_3$): δ 16.81 and 19.38 (—CH(C$\underline{H}_3$)$_2$), 24.44 (—CH$_2$—C$\underline{H}_2$—C$\underline{H}_2$—CH$_2$—), 28.67 (2-$\underline{C}$H$_3$), 30.95 (—$\underline{C}$H(CH$_3$)$_2$), 41.39 (—$\underline{C}$H$_2$—CH$_2$—CH$_2$—$\underline{C}$H$_2$—), 52.11 (—OCH$_3$), 58.40 (5-$\overline{C}$),61.10 (2-C), 161.71 and 165.41 (C=N). C$_{24}$H$_{42}$N$_4$O$_4$ Calc.: C; 63.97 H; 9.39 Found: C; 63.91 H; 9.32

1,5-Bis-[(2S, 5R)-2,5-dihydro-3,6-dimethoxy-5-isopropyl-2-methyl-2-pyrazinyl]pentane The general procedure outlined above was used. The reagents used were (5R,2R,S)-2,5-dihydro-3,6-dimethoxy-5-isopropyl-2-methylpyrazine (4.2 g, 21.19 mmol), THF (180 ml), DMEU (4.82 g, 42.38 mmol), n-butyllithium (1.6M; 14.57 ml, 23.31 mmol) and 1,5-dibromopentane (2.44 g, 10.60 mmol) in THF (25 ml). Stirring was continued for 18 h at −78° C. The excess of dibromopentane was removed from the crude mixture by evaporation at 40°

C./0.01 torr. The product was purified by flash-chromatography on silica gel 60 using hexane:diethyl ether (20:1).

Yield 2.96 g (60%). mp. 65.2° C. (nitromethane) Capillary GLC; d.e. 88.4% IR (KBr): 1690 cm$^{-1}$ (C=N). $^1$H NMR (CDCl$_3$: δ 0.66 and 1.07(2 d; J 6.9 Hz; 6H; —CH(CH$_3$)$_2$), 0.79–1.27 (m; 6H; —CH$_2$—CH$_2$—CH$_2$—CH$_2$—CH$_2$—), 1.30(s;3H; 2-CH$_3$), 1.38–1.90 (m; 4H; —CH$_2$—CH$_2$—CH$_2$—CH$_2$—CH$_2$—CH$_2$—), 2.25(dsp;J1 6.9 Hz, J2 3.4 Hz; 1H, —CH(CH$_3$)$_2$), 3.65(s; 6H; —OCH$_3$), 3.93 (d;J 3.4 Hz; 1H;5-H). $^{13}$C NMR(CDCl$_3$): δ 16.73 and 19.30 (—CH(CH$_3$)$_2$), 24.22 (—CH$_2$—CH$_2$—CH$_2$—), 28.59 (2-CH$_3$), 29.36 (—CH$_2$—CH$_2$—CH$_2$—), 30.89 (—CH(CH$_3$)$_2$), 41.19 (—CH$_2$—CH$_2$—CH$_2$—), 52.03 (—OCH3), 58.36 (2-C), 61.03 (5-C), 161.57 and 165.43 (C=N).

1,6-Bis-[(2S, 5R)-2,5-dihydro-3,6-dimethoxy-5-isopropyl-2-methyl-2-pyrazinyl]hexane The general procedure outlined above was used. The reagents used were (5R,2R, S)-2,5-dihydro-3,6-dimethoxy-5-isopropyl-2-methylpyrazine (3.8 g, 19.17 mmol), THF (170 ml), DMEU (4.38 g, 38.34 mmol), n-butyllithium (1.6 M; 13.18 ml, 21.09 mmol) and 1,6-dibromohexane (2.34 g, 9.59 mmol) in THF (40 ml). Stirring was continued for 15 h at −78° C. The excess of dibromohexane was removed from the crude mixture by evaporation at 40° C./0.01 torr. The product was purified by flash-chromatography on silica gel 60 using hexane:diethyl ether (20:1).

Yield 3.35 g (73%). mp. 51° C. (nitromethane) Capillary GLC; d.e. 82.0% IR (KBr): 1690 cm$^{-1}$ (C=N). $^1$H NMR (CDCl$_3$): δ 0.66 and 1.07(2 d; J 6.9 Hz; 6H; —CH(CH$_3$)$_2$), 0.79–1.27 (m; 4H; —CH$_2$—CH$_2$—CH$_2$—CH$_2$—CH$_2$—), 1.30 (s;3H; 2-CH$_3$), 1.33–1.80 (m; 2H; —CH$_2$—CH$_2$—CH$_2$—CH$_2$—CH$_2$—CH$_2$—), 2.25(dsp;J1 6.9 Hz, J2 3.4 Hz; 1H, —CH(CH$_3$)$_2$), 3.65(s; 6H; —OCH$_3$), 3.93 (d;J 3.4 Hz 1H;5-H). $^{13}$C NMR(CDCl$_3$): δ 16.82 and 19.36 (—CH(CH$_3$)$_2$), 24.29 (—CH$_2$—CH$_2$—CH$_2$—), 28.65 (2-CH$_3$), 29.40 (—CH$_2$—CH$_2$—CH$_2$—), 30.97 (—CH (CH$_3$)$_2$), 41.35 (—CH$_2$—CH$_2$—CH$_2$—), 52.10 (—OCH$_3$), 58.44 (2-C), 61.10 (5-C), 161.67 and 165.50 (C=N).

Bis-[(2S, 5R)-2,5-dihydro-3,6-dimethoxy-5-isopropyl-2-methyl-2-pyrazinyl]

The general procedure outlined above was used to effect bromination by 1,2-dibromoethane and dimerisation of the heterocycle. The reagents used were (5R,2R,S)-2,5-dihydro-3,6-dimethoxy-5-isopropyl-2-methylpyrazine (3.3 g, 16.65 mmol), THF (200 ml), DMEU (3.80 g, 33.29 mmol), n-butyllithium (1.6M; 11.45 ml, 18.32 mmol) and 1,2-dibromoethane (3.13 g, 16.65 mmol) in THF (30 ml). Stirring was continued for 10 h at −78° C. The excess of dibromohexane was removed from the crude mixture by evaporation at 40° C./0.01 torr. The product was purified by flash-chromatography on silica gel 60 using hexane:diethyl ether (15:1).

Yield 2.04 g (62%). mp. 65°–66° C. IR (KBr): 1690 cm$^{-1}$ (C=N). $^1$H NMR (CDCl$_3$: δ 0.59 and 0.99(2 d; J 6.9 Hz; 6H; —CH(CH$_3$)$_2$),1.53 (s;3H; 2-CH$_3$), 2.18(dsp;J1 6.9 Hz, J2 3.4 Hz; 1H, —CH(CH$_3$)$_2$), 3.51 and 3.65 (2 s; 12H; —OCH$_3$), 3.87 (d;J 3.4 Hz; 1H;5-H). $^{13}$C NMR(CDCl$_3$): δ 16.50 and 19.14 (—CH(CH$_3$)$_2$), 23.35 (2-CH$_3$), 30.68 (—CH(CH$_3$)$_2$), 51.67 and 51.96 (—OCH3), 59.82 (5-C), 64.93 (2-C), 161.95 and 163.92 (C=N). C$_{20}$H$_{34}$N$_4$O$_4$ Calc: C; 60.73 H; 8.63 Found: C; 60.89 H; 8.69

EXAMPLE 2

Monoalkylation and isolation of intermediate (2S, 5R)-2-Bromomethyl-2,5-dihydro-3,6-dimethoxy-5-isopropyl-2-methylpyrazine The general procedure outlined above was used. The reagents used were (5R,2R,S)-2,5-dihydro-3,6-dimethoxy-5-isopropyl-2-methylpyrazine (2.8 g, 14.13 mmol), THF (220 ml), DMEU (3.23 g, 28.26 mmol), n-butyllithium (1.6M; 9.71 ml, 15.54 mmol) and dibromomethane (1.23 g, 7.07 mmol) in THF (30 ml). Stirring was continued for 18 h at −78° C. The excess of dibromomethane was removed from the crude mixture by evaporation at 40° C./0.01 torr. The product was purified by flash-chromatography on silica gel 60 using hexane:diethyl ether (15:1).

Yield 3.17 g (77%). IR (KBr): 1690 cm$^{-1}$ (C=N). $^1$H NMR (CDCl$_3$: δ 0.68 and 1.08(2 d; J 7.3 Hz; 6H; —CH (CH$_3$)$_2$),1.45 (s;3H; 2-CH$_3$), 2.29(dsp;J1 7.3 Hz, J2 3.7 Hz; 1H, —CH(CH$_3$)$_2$), 3.39 and 3.75 (dd, J1 12.4 Hz, J2 10.4 Hz;2H; —CH$_2$Br), 3.67 and 3,71 (2s; 6H; —OCH$_3$), 4.03 (d;J 3.7 Hz; 1H;5-H). $^{13}$C NMR(CDCl$_3$): δ 16.77 and 19.28 (—CH(CH$_3$)$_2$), 26.52 (2-CH$_3$), 30.83(—CH(CH$_3$)$_2$), 43.04 (—CH$_2$—Br), 52.40 and 52.48 (—OCH$_3$), 58.32 (2-C), 61.00 (5-C), 161.71 and 165.41 (C=N).

(2S, 5R)-2-(2-Chloroethyl)-2,5-dihydro-3,6-dimethoxy-5-isopropyl-2-methylpyrazine The general procedure outlined above was used. The reagents used were (5R,2R, S)-2,5-dihydro-3,6-dimethoxy-5-isopropyl-2-methylpyrazine (3.5 g, 17.66 mmol), THF (200 ml), DMEU (4.03 g, 35.31 mmol), n-butyllithium (1.6M; 12.14 ml, 19.43 mmol) and 1-bromo-2-chloroethane (6.33 g, 44.15 mmol) in THF (30 ml). Stirring was continued for 18 h at −78° C. The excess of 1-bromo-2-chloroethane was removed from the crude mixture by evaporation at 40° C./0.01 torr. The product was purified by flash-chromatography on silica gel 60 using hexane; diethyl ether (20:1).

Yield 2.44 g (53%). Capillary GLC: d.e. 90% IR (KBr): 1690 cm$^{-1}$ (C=N). $^1$H NMR (CDCl$_3$): δ 0.68 and 1.06(2 d; J 7.7 Hz; 6H; —CH(CH$_3$)$_2$),1.34 (s;3H; 2-CH$_3$), 1.97–2.37 (m; 3H; —CH$_2$—CH$_2$Cl and —CH(CH$_3$)$_2$), 3.21 and 3.38 (m; 2H; —CH$_2$—CH$_2$Cl), 3.66 and 3.67 (2s; 6H; —OCH$_3$), 3.95 (d;J 3.7 Hz; H;5-H). $^{13}$C NMR(CDCl$_3$): δ 16.91 and 19.30 (—CH(CH$_3$)$_2$), 28.65 (2-CH$_3$), 31.00(—CH(CH$_3$)$_2$), 40.51 (—CH$_2$—CH$_2$—Cl), 43.72 (—CH$_2$—CH$_2$—Cl), 52.19 and 52.32 (—OCH3), 57.29 (2-C), 61.08 (5-C), 162.49 and 164.31 (C=N).

(2S, 5R)-2-(2-Bromoethyl)-2,5-dihydro-3,6-dimethoxy-5-isopropyl-2-methylpyrazine (2S,5R)-2-(2-Chloroethyl)-2,5-dihydro-3,6-dimethoxy-5-isopropyl -2-methylpyrazine produced as above (1.0 g, 3.83 mmol) and NaBr (0.47 g, 4.60 mmol) in DMF (30 ml) was stirred at 70° C. for 12 h. The solvent was then removed at 40° C./0.01 torr and the product purified by flash-chromatography on silica gel 60 using hexane:diethyl ether (20:1).

Yield 1.03 g (88%). IR (KBr): 1690 cm$^{-1}$ (C=N). $^1$H NMR (CDCl$_3$): δ 0.68 and 1.06(2 d; J 7.7 Hz; 6H; —CH(CH$_3$)$_2$), 1.34 (s;3H; 2-CH$_3$), 1.97–2.37 (m; 3H; —CH$_2$—CH$_2$Cl and —CH(CH$_3$)$_2$, 3.21 and 3.38 (m; 2H; —CH$_2$—CH$_2$Cl), 3.66 and 3.67 (2s; 6H; —OCH$_3$), 3.95 (d;J 3.7 Hz; 1H;5-H). $^{13}$C NMR(CDCl$_3$): δ 16.91 and 19.30 (—CH(CH$_3$)$_2$), 28.65 (2-CH$_3$), 31.00(—CH(CH$_3$)$_2$), 40.51 (—CH$_2$—CH$_2$—Cl), 43.72 (—CH$_2$—CH$_2$—Cl), 52.19 and 52.32 (—OCH$_3$), 57.29 (2-C), 61.08 (5-C), 162.49 and 164.31 (C=N).

(2S, 5R)-2-(2-Iodoethyl)-2,5-dihydro-3,6-dimethoxy-5-isopropyl-2-methylpyrazine (2S,5R)-2-(2-Chloroethyl)-2,5-dihydro-3,6-dimethoxy-5-isopropyl-2-methylpyrazine produced as above (1.7 g, 6.52 mmol) and NaI (0.47g, 7.82 mmol) in DMF (30 ml) was stirred at 70° C. for 12 h. The solvent was then removed at 40° C./0.01 torr and the product purified by flash-chromatography on silica gel 60 using hexane;diethyl ether (20:1).

Yield 1.03 g (88%). IR (KBr): 1690 cm$^{-1}$ (C=N). $^1$H NMR (CDCl$_3$): δ 0.66 and 1.05(2 d; J 7.7 Hz; 6H; —CH(CH$_3$)$_2$), 1.30 (s;3H; 2-CH$_3$), 2.12–2.49 (m; 3H; —CH$_2$—CH$_2$I and —CH(CH$_3$)$_2$), 2.76–2.98 (m; 2H; —CH$_2$—CH$_2$I), 3.65 and 3.66 (2s; 6H; —OCH$_3$), 3.93 (d;J 4.0 Hz; 1H;5-H). $^{13}$C NMR(CDCl$_3$): δ 0.92 (—CH$_2$—CH$_2$I), 16.89 and 19.30 (—CH(CH$_3$)$_2$), 28.30 (2-CH$_3$), 31.00 (—CH(CH$_3$)$_2$), 45.65 (—CH$_2$—CH$_2$—I), 52.23 and 52.36 (—OCH$_3$), 59.77 (2-C), 61.16 (5-C), 162.59 and 163.96 (C=N).

EXAMPLE 3

Dimer formation from monoalkylated intermediate 1,2-Bis-[(2S, 5R)-2,5-dihydro-3,6-dimethoxy-5-isopropyl-2-methyl-2-pyrazinyl]ethane The general procedure outlined above was used. The reagents used were (5R,2R, S)-2,5-dihydro-3,6-dimethoxy-5-isopropyl-2-methylpyrazine (2.0 g, 10.08 mmol), THF (70 ml), DMEU (2.30 g, 20.16 mmol), n-butyllithium (1.6M; 6.94 ml, 11.1 mmol) and (2S,5R)-(2-bromoethyl)-2,5-dihydro-3,6-dimethoxy-5-isopropyl-2-methylpyrazine (1.09 g, 5.04 mmol) in THF (30 ml). Stirring was continued for 18 h at −78° C. The product was purified by flash-chromatography on silica gel 60 using hexane;diethyl ether (20:1).

Yield 2.44 g (62%). mp. 96° C. Capillary GLC: d.e. 96% IR (KBr): 1690 cm$^{-1}$ (C=N). $^1$H NMR (CDCl$_3$): δ 0.65 and 1.05(2 d; J 7.7 Hz; 6H; —CH(CH$_3$)$_2$),1.28 (s;3H; 2-CH$_3$), 1.38–1.80 (m; 4H; —CH$_2$—CH$_2$—) 2.24 (dsp; J1 7.7 Hz, J2 3.7 Hz; 1H, —CH(CH$_3$)$_2$), 3.63 (s; 6H; —OCH$_3$), 3.90 (d;J 3.7 Hz; 1H;5-H). $^{13}$C NMR(CDCl$_3$): δ 16.72 and 19.30 (—CH(CH$_3$)$_2$), 24.36 (—CH$_2$—CH$_2$—), 28.61 (2-CH$_3$), 30.87 (—CH(CH$_3$)$_2$), 41.31 (—CH$_2$—CH$_2$—), 52.00 and 52.02 (—OCH$_3$), 58.31 (5-C), 61.01 (2-C), 161.62 and 165.32 (C=N).

EXAMPLE 4

Hydrolysis (S,S-2,3-Diamino-2,3-dimethylbutanedioic acid dimethyl diester 1,2-Bis-[(2S, 5R)-2,5-dihydro-3,6-dimethoxy-5-isopropyl-2-methyl-2-pyrazinyl] (0.67 g, 1.70 mmol) was dissolved in acetonitrile (20 ml), 0.5N HCl (20.4 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.29 g (82%).

(S,S)-2,5-Diamino-2,5-dimethylhexanedioic acid dimethyl diester 1,2-Bis-[(2S, 5R)-2,5-dihydro-3,6-dimethoxy-5-isopropyl-2-methyl-2-pyrazinyl]ethane (0.82 g, 1.94 mmol) was dissolved in acetonitrile (25 ml), 0.5N HCl (23.3 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.41 g (91%). $^1$H NMR (CDCl$_3$): δ 1.08–1.24(m; 1H; —CH$_2$—), 1.30(s; 3H; —CH$_3$), 1.42–1.76 (m; 3H; —NH$_2$ and —CH$_2$—), 3.69(s; 3H; —OCH$_3$).

(S,S)-2,6-Diamino-2,6-dimethylheptanedioic acid dimethyl diester 1,3-Bis-[(2S, 5R)-2,5-dihydro-3,6-dimethoxy-5-isopropyl-2-methyl-2-pyrazinyl]propane (0.77 g, 1.76 mmol) was dissolved in acetonitrile (20 ml), 0.5N HCl (21.2 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.39 g (91%). $^1$H NMR (CDCl$_3$): δ 1.02–1.34(m; 2H; —CH$_2$—), 1.30(s; 3H; —CH$_3$), 1.34–1.82 (m; 3H; —NH$_2$ and —CH$_2$—), 3.69(s; 3H; —OCH$_3$).

(S,S)-2,7-Diamino-2,7-dimethyloctanedioic acid dimethyl diester 1,4-Bis-[(2S, 5R)-2,5-dihydro-3,6-dimethoxy-5-isopropyl-2-methyl-2-pyrazinyl]butane (0.90 g, 2.00 mmol) was dissolved in acetonitrile (24 ml), 0.5N HCl (24 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.48 g (92%). $^1$H NMR (CDCl$_3$): δ 1.02–1.28(m; 2H; —CH$_2$—), 1.29(s; 3H; —CH$_3$), 1.42–1.85 (m; 4H; —NH$_2$ and —CH$_2$—), 3.69(s; 3H; —OCH$_3$). $^{13}$C NMR (CDCl$_3$); δ 24.36 (—CH$_2$—CH$_2$—), 26.27 (—CH$_3$), 40.90 (—CH$_2$—CH$_2$—), 52.05 (—OCH$_3$), 57.65 (—C—NH$_2$), 178.00 (—COOCH3).

(S,S)-2,8-Diamino-2,8-dimethylnonanedioic acid dimethyl diester 1,5-Bis-[(2S, 5R)-2,5-dihydro-3,6-dimethoxy-5-isopropyl-2-methyl-2-pyrazinyl]pentane (0.75 g, 1.61 mmol) was dissolved in acetonitrile (20 ml), 0.5N HCl (19.4 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.34 g (78%). $^1$H NMR (CDCl$_3$): δ 0.98–1.38(m; 3H; —CH$_2$—), 1.28(s; 3H; —CH$_3$), 1.38–1.81 (m; 4H; —NH$_2$ and —CH$_2$—), 3.71(s; 3H; —OCH$_3$). $^{13}$C NMR (CDCl$_3$); δ 23.97 (—CH$_2$—CH$_2$—CH$_2$—), 26.31 (—CH$_3$), 29.95 (—CH$_2$—CH$_2$—CH$_2$—), 40.98 (—CH$_2$—CH$_2$—CH$_2$—), 52.04 (—OCH$_3$), 57.69 (—C—NH$_2$), 178.08 (—COOCH$_3$).

(S,S)-2,9-Diamino-2,9-dimethyldecanedioic acid dimethyl diester 1,6-Bis-[(2S, 5R)-2,5-dihydro-3,6-dimethoxy-5-isopropyl-2-methyl-2-pyrazinyl]hexane (0.87 g, 1.82 mmol) was dissolved in acetonitrile (25 ml), 0.5N HCl (21.8 ml) was added dropwise, and the solution stirred at room temperature overnight. Ammonia solution was added until the solution reached a pH of 11. The mixture was then extracted with chloroform and dried (MgSO$_4$). The resultant chloroform solution was evaporated and the valine methyl ester removed from the residual product by bulb-to-bulb distillation at 35° C./0.05 torr.

Yield 0.43 g (82%). $^1$H NMR (CDCl$_3$): δ 1.00–1.40(m; 4H; —CH$_2$—), 1.30(s; 3H; —CH$_3$), 1.40–1.83 (m; 4H; —NH$_2$ and —CH$_2$—), 3.69(s; 3H; —OCH$_3$). $^{13}$C NMR (CDCl$_3$); δ 24.04 (—CH$_2$—CH$_2$—CH$_2$—), 26.34 (—CH$_3$), 29.58 (—CH$_2$—CH$_2$—CH$_2$—), 41.05 (—CH$_2$—CH$_2$—CH$_2$—), 52.03 (—OCH$_3$), 57.73 (—C—NH$_2$), 178.14 (—COOCH3).

EXAMPLE 5

N-Protection (S,S)-2,5-Bis-(9-fluorenylmethyloxycarbonylamino)2,5-dimethylhexanedioic acid dimethyl diester Fmoc-Cl (1.33 g, 5.16 mmol) and 1N NaHCO$_3$ (5.2 ml) were simultaneously added gradually with stirring to a solution of (S,S)-2,5-diamino-2,5-dimethylhexanedioic acid dimethyl diester (400 mg, 1.72 mmol) in dioxane (30 ml) and the mixture stirred at room temperature for 20 h. The dioxane was removed by distillation and the residue extracted with chloroform. The chloroform solution was then washed, dried (MgSO$_4$), and evaporated down. The title compound was isolated after flash-chromatography using hexane: EtOAc from 4:1 to 2:1.

Yield 873 mg (75%). $^1$H NMR (CDCl$_3$) δ 1.56 (s; 3H; —CH$_3$), 1.03, 1.24, 1.73 and 2.11 (br s; 4H; —CH$_2$—CH$_2$—), 3.74 (br s; 3H; —OCH$_3$), 4.22 (t; J 6.2 Hz; —Fmoc), 4.37 (br s; 2H; —CH$_2$—Fmoc), 5.59 (br s; 1H; —NH—Fmoc), 7.23-7.81 (m; 8H; —Fmoc). $^{13}$C NMR (CDCl$_3$): δ 23.36, 23.90, 36.57, 47.21, 52.68, 59.88, 66.32, 119.90, 124.94, 126.97, 127.90, 141.27, 143.87, 174.66.

(S,S)-2,6-Bis-(9-fluorenylmethyloxycarbonylamino)-2,6-dimethylheptanedioic acid dimethyl diester Fmoc-Cl (0.95 g, 3.66 mmol) and 1N NaHCO$_3$ (3.7 ml) were simultaneously added gradually with stirring to a solution of (S,S)-2,6-diamino-2,6-dimethylheptanedioic acid dimethyl diester (300 mg, 1.22 mmol) in dioxane (30 ml) and the mixture stirred at room temperature for 20 h. The dioxane was removed by distillation and the residue extracted with chloroform. The chloroform solution was then washed, dried (MgSO$_4$), and evaporated down. The title compound was isolated after flash-chromatography using hexane:EtOAc from 4:1 to 2:1.

Yield 632 mg (75%). $^1$H NMR (CDCl$_3$) δ 1.56 (s; 3H; —CH$_3$), 1.03, 1.24, 1.73 and 2.11. (br s; 4H; —CH$_2$—CH$_2$—), 3.74 (br s; 3H; —OCH$_3$), 4.22 (t; J 6.2 Hz; —Fmoc), 4.37 (br s; 2H; —CH$_2$—Fmoc), 5.59 (br s; 1H; —NH—Fmoc), 7.23-7.81 (m; 8H; —Fmoc). $^{13}$C NMR (CDCl$_3$): δ 23.36, 36.31, 47.16, 52.66, 59.90, 66.43, 119.93, 124.94, 127.02, 127.63, 141.26, 143.85, 174.51.

(S,S)-2,7-Bis-(9-fluorenylmethyloxycarbonylamino)-2,7-dimethyloctanedioic acid dimethyl diester Fmoc-Cl (1.20 g, 4.62 mmol) and 1N NaHCO$_3$ (4.6 ml) were simultaneously added gradually with stirring to a solution of (S,S)-2,7-diamino-2,7-dimethyloctanedioic acid dimethyl diester (400 mg, 1.54 mmol) in dioxane (30 ml) and the mixture stirred at room temperature for 20 h. The dioxane was removed by distillation and the residue extracted with chloroform. The chloroform solution was then washed, dried (MgSO$_4$), and evaporated down. The title compound was isolated after flash-chromatography using hexane:EtOAc from 4:1 to 2:1.

Yield 955 mg (88%). $^1$H NMR (CDCl$_3$) δ 1.59 (s; 3H; —CH$_3$), 1.02, 1.55, 1.75 and 2.13 (br s; 4H; —CH$_2$—CH$_2$—), 3.74 (br s; 3H; —OCH$_3$), 4.21 (t; J 6.2 Hz; —Fmoc), 4.37 (br s; 2H ; —CH$_2$—Fmoc), 5.59 (br s; 1H; —NH—Fmoc), 7.21-7.79 (m; 8H; —Fmoc). $^{13}$C NMR (CDCl$_3$): δ 23.36, 23.90, 36.56, 47.20, 52.68, 59.87, 66.32, 119.90, 124.93, 126.96, 127.59, 141.26, 143.86, 174.65.

(S,S)-2,8-Bis-(9-fluorenylmethyloxycarbonylamino)-2,8-dimethylnonanedioic acid dimethyl diester Fmoc-Cl (0.85 g, 3.27 mmol) and 1N NaHCO$_3$ (3.3 ml) were simultaneously added gradually with stirring to a solution of (S,S)-2,8-diamino-2,8-dimethylnonanedioic acid dimethyl diester (300 mg, 1.09 mmol) in dioxane (30 ml) and the mixture stirred at room temperature for 20 h. The dioxane was removed by distillation and the residue extracted with chloroform. The chloroform solution was then washed, dried (MgSO$_4$), and evaporated down. The title compound was isolated after flash-chromatography using hexane:EtOAc from 4:1 to 2:1.

Yield 478 mg (61%). $^1$H NMR (CDCl$_3$) δ 1.55. (br s; 3H; —CH$_3$), 1.18, 1.78 and 2.17 (br s; 5H; —CH$_2$—CH$_2$—CH$_2$—), 3.69 (br s; 3H; —OCH$_3$), 4.20 (t; J 6.2 Hz; —Fmoc), 4.35 (br s; 2H; —CH$_2$—Fmoc), 5.63 (br s; 1H; —NH—Fmoc), 7.23-7.79 (m; 8H; —Fmoc). $^{13}$C NMR (CDCl$_3$): δ 23.39, 23.86, 29.15, 36.61, 47.21, 52.66, 59.95, 66.31, 119.90, 124.95, 126.95, 127.59, 141.27, 143.89, 174.72.

(S,S)-2,9-Bis-(9-fluorenylmethyloxycarbonylamino)-2,9-dimethyldecanedioic acid dimethyl diester Fmoc-Cl (1.08 g, 4.17 mmol) and 1N NaHCO$_3$ (4.2 ml) were simultaneously added gradually with stirring to a solution of (S,S)-2,9-diamino-2,9-dimethyldecanedioic acid dimethyl diester (400 mg, 1.39 mmol) in dioxane (30 ml) and the mixture stirred at room temperature for 20 h. The dioxane was removed by distillation and the residue extracted with chloroform. The chloroform solution was then washed, dried (MgSO$_4$), and evaporated down. The title compound was isolated after flash-chromatography using hexane:EtOAc from 4:1 to 2:1.

Yield 560 mg (55%). $^1$H NMR (CDCl$_3$) δ 1.55 (s; 3H; —CH$_3$), 1.01, 1.22, 1.77 and 2.12 (br s; 6H; —CH$_2$—CH$_2$—CH$_2$—), 3.74 (br s; 3H; —OCH$_3$), 4.21 (t; J 6.2 Hz; —Fmoc), 4.36 (br s; 2H; —CH$_2$—Fmoc), 5.61 (br s; 1H; —NH—Fmoc), 7.21-7.79 (m; 8H; —Fmoc). $^{13}$C NMR (CDCl$_3$): δ 23.35, 23.96, 29.15, 36.71, 47.22, 52.64, 59.98, 66.30, 119.89, 124.94, 126.95, 127.58, 141.27, 143.89, 174.78.

EXAMPLE 6

Ester hydrolysis (S,S)-2,5-Bis-(9-fluorenylmethyloxycarbonylamino)-2,5-dimethylhexanedioic acid 6N HCl (0.6 ml, 3.55 mmol) was added to a solution of (S,S)-2,5-bis-(9-fluorenylmethyloxycarbonylamino)-2,5-dimethylhexanedioic acid dimethyl diester (600 mg, 0.887 mmol) in dioxane (10 ml) and the resultant solution heated at 90° C. for 24 h. The dioxane was then distilled off and the residue extracted with chloroform (2×20 ml). The chloroform solution was washed, dried (MgSO$_4$), and evaporated down. The title compound was isolated after flash-chromatography using hexane:EtOAc:HOAc 1:1:0.1

White powder, yield 409 mg (71%) $^1$H NMR (DMSO-d$_6$): δ 1.13 (s(br); 1H; —CH$_2$—CH$_2$—CH$_2$—), 1.30 (s; 3H; —CH$_3$), 1.68 (s(br); 1H; —CH$_2$—CH$_2$—), 4.22 (m; 3H; —Fmoc), 7.21-7.96 (m; 9H; —Fmoc and —NH), 12.40 (s(br); 1H; —COOH). $^{13}$C NMR (DMSO-d$_6$); δ 22.97, 23.98, 37.09, 44.00, 47.17, 58.76, 65.59, 120.46, 125.63, 127.44, 127.98, 141.10, 144.27, 155.01, 175.71.

(S,S)-2,7-Bis-(9-fluorenylmethyloxycarbonylamino)-2,7-dimethyloctanedioic acid

6N HCl (0.76 ml, 4.54 mmol) was added to a solution of (S,S)-2,7-bis-(9-fluorenylmethyloxycarbonylamino)-2,7-dimethyloctanedioic acid dimethyl diester (800 mg, 1.14 mmol) in dioxane (10 ml) and the resultant solution heated at 90° C. for 24 h. The dioxane was then distilled off and the residue extracted with chloroform (2×20 ml). The chloroform solution was washed, dried (MgSO$_4$), and evaporated down. The title compound was isolated after flash-chromatography using hexane:EtOAc:HOAc 1:1:0.1

White powder, yield 679 mg (88%) $^1$H NMR (DMSO-d$_6$):
δ 1.13 (s(br); 1H; —CH$_2$—CH$_2$—CH$_2$—), 1.30 (s 3H;
—CH$_3$), 1.68 (s(br); 1H; —CH$_2$—CH$_2$—), 4.22 (m; 3H;
—Fmoc), 7.21–7.96 (m; 9H; —Fmoc and —NH), 12.40
(s(br); 1H; —COOH). $^{13}$C NMR (DMSO-d$_6$); δ 22.97,
23.98, 37.09, 44.00, 47.17, 58.76, 65.59, 120.46, 125.63,
127.44, 127.98, 141.10, 144.27, 155.01, 175.71.

(S,S)-2,8-Bis-(9-fluorenylmethyloxycarbonylamino)-2,8-dimethylnonanedioic acid

6N HCl (0.37 ml, 2.23 mmol) was added to a solution of (S,S)-2,8-bis-(9-fluorenylmethyloxycarbonylamino)-2,8-dimethylnonanedioic acid dimethyl diester (400 mg, 0.556 mmol) in dioxane (10 ml) and the resultant solution heated at 90° C. for 24 h. The dioxane was then distilled off and the residue extracted with chloroform (2×20 ml). The chloroform solution was washed, dried (MgSO$_4$), and evaporated down. The title compound was isolated after flash-chromatography using hexane:EtOAc:HOAc 1:1:0.1

White powder, yield 280 mg (73%) $^1$H NMR (DMSO-d$_6$):
δ 1.22 (s(br); 3H; —CH$_2$—CH$_2$), 1.31 (s; 3H; —CH$_3$), 1.69
(s(br); 2H; —CH$_2$—CH$_2$—), 4.22 (m; 3H; —Fmoc),
7.17–7.96 (m; 9H; —Fmoc and —NH), 12.14 (s(br); 1H;
—COOH). $^{13}$C NMR (DMSO-d$_6$); δ 23.05, 23.66, 36.95,
47.18, 58.83, 65.57, 120.46, 125.63, 127.44, 127.98, 141.11,
144.28, 155.95, 175.77.

(S,S)-2,9-Bis-(9-fluorenylmethyloxycarbonylamino)-2,9-dimethyldecanedioic acid

6N HCl (0.45 ml, 2.73 mmol) was added to a solution of (S,S)-2,9-bis-(9-fluorenylmethyloxycarbonylamino)-2,9-dimethyldecanedioic acid dimethyl diester (500 mg, 0.682 mmol) in dioxane (10 ml) and the resultant solution heated at 90° C. for 24 h. The dioxane was then distilled off and the residue extracted with chloroform. (2×20 ml). The chloroform solution was washed, dried (MgSO$_4$), and evaporated down. The title compound was isolated after flash-chromatography using hexane: EtOAc:HOAc 1:1:0.1

White powder, yield 375 mg (78%) $^1$H NMR (DMSO-d$_6$):
δ 1.16 (s(br); 4H; —CH$_2$—CH$_2$—CH$_2$), 1.31 (s; 3H;
—CH$_3$), 1.70 (s(br); 2H; —CH$_2$—CH$_2$—CH$_2$), 4.23 (m;
3H; —Fmoc), 7.18–8.04 (m; 9H; —Fmoc and —NH), 12.20
(s(br); 1H; —COOH). $^{13}$C NMR (DMSO-d$_6$); δ 21.51,
23.19, 29.31, 36.83, 47.20, 58.95, 65.43, 120.46, 125.59,
127.42, 127.97, 141.12, 144.31, 154.80, 172.37

EXAMPLE 7

Preparation of (Pic-Ser-Asp)$_2$-α,α'-Me$_2$-Sub(Lys-OH)$_2$

FmocLys(Boc)-Sasrin-Resin (0.6 mmol, 1.0 g) was deprotected for 10 mins under nitrogen in 20% piperidine/DMF. The resin was then washed well with DMF (8×15 ml).

(S,S)-Di-N-Fmoc-2,7-diamino-2,7-dimethylsuberic acid (0.15 mmol, 0.1 g) was weighed into a clean vial along with PyBOP (0.3 mmol, 0.16 g) and HOBt (0.3 mmol, 0.04 g). DMF (10 ml) was then added followed by NMM (0.45 mmol, 0.05 ml) and the mixture stirred for 4 mins. The activated amino acid was transferred to the deprotected resin in the nitrogen bubbler. At regular intervals resin samples were removed and subjected to loading analysis.

After 22 h coupling, a resin sample (10 mg) was removed from the reaction vessel. The sample was washed well with DMF (4×10 ml), DCM (3×10 ml) and diethyl ether (3×10 ml), then dried for 3 h in a vacuum dessicator. Two samples of resin were then accurately weighed into clean UV cells and 3 ml of 20% piperidine added. Both cuvettes were sonicated for 1 min and the resin allowed to settle before-reading the absorbance value at 290 nm. The level of incorporation can be read from a correlation graph obtained by spectrophotometry of a standard solution containing Fmoc/piperidine.

Average absorbance value = 0.7 or 40% amino acid incorporation

= 0.12 mmol/g

The resin in the nitrogen bubbler was then washed well with DMF (5×10 ml) and unreacted acid functions treated with a second batch of PyBoP, HOBt and NMM in 10 ml of DMF for a further 3 h.

After several DMF washes (5×10 ml) all remaining lysine residues were capped with 10% acetic anhydride in DMF for 10 mins.

The resin was washed with DMF (5×10 ml) then Fmoc deprotected 3 times in 20% piperidine for 10, 5 and 5 mins respectively followed by 5×19 ml DMF washes.

FmocAsp(OtBu)OH (2 mmol, 0.82 g) was weighed into a clean vial along with PyBOP (2.0 mmol, 1.04 g) and HOBt (2.0 mmol, 0.27 g). DMF (10 ml) was then added followed by NMM (3.0 mmol, 0.33 ml) and the mixture stirred for 4 mins. The activated amino acid was transferred to the deprotected resin in the nitrogen bubbler. Once again resin samples were removed and subjected to loading analysis. After 16 h acylation the incorporation of FmocAsp(OtBu) OH onto the resin had reached 97% and so the coupling was terminated.

FmocSer(tBu)OH and PicOH were incorporated using standard PyBOP couplings and ninhydrin monitoring.

Cleavage of the peptide from the resin was carried out in 5% aqueous TFA for 1 h. The crude peptide was precipitated and triturated with diethyl ether and air dried.

Purification of the crude peptide (40 mg) by preparative HPLC (Vydac TP1002, 20 cm column) using a 0 to 20% B (B=40% acetonitrile) gradient over 150 mins yielded 6 mg of the title peptide after lyophilisation; FAB-MS: M$^+$ 1099 (actual 1199).

HPLC (Vydac 218TP54, 0 to 30% B over 20 mins); Retention time=17.9 mins.

EXAMPLE 8

Preparation of (pyro-Glu-Glu-Asp)$_2$-α-Me-C4-(Lys-OH)$_2$
C4=2,7-diamino-2,7-dimethyloctanedioic acid.
Prepared analogously to Example 7.
FAB-MS: Expected 1198; found 1199.4. HPLC: 0 to 30% B; B=40% MeCN in 0.1% TFA in water (Vydac): retention time 17.9 mins.

EXAMPLE 9

Preparation of (pyro-Glu-Glu-Asp)$_2$-α-Me-C2-(Lys-OH)$_2$
C2=2,5-diamino-2,5-dimethylhexanedioic acid.
Prepared analogously to Example 7.
FAB-MS: Expected 1198; found HPLC: 0 to 30% B; B=40% MeCN in 0.1% TFA in water.

We claim:

1. Peptide compounds of formula I:

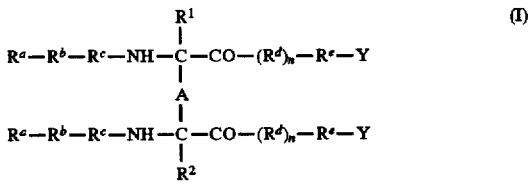

wherein
R$^1$ and R$^2$ independent represent hydrogen atoms or C$_{1-4}$-alkyl groups with the proviso that R$^1$ and R$^2$ may not simultaneously represent hydrogen atoms;

A represents a carbon-carbon bond, a saturated or unsaturated $C_{1-8}$-alkylene or aralkylene group, cis or trans $-CH_2-CH=CH-CH_2-$, $-CH_2-CH\equiv C-CH_2-$, $-(CH_2)_p-Z-(CH2)q$ wherein Z is O, S or $S_2$ and p and q independently represent 1 or 2, or $-(CH_2)_r-C_6H_4-(CH_2)_s$ wherein r and s independently represent 0 or 1;

each $R^a$ independently represents pyroglutamic acid (pGlu), pyridine-2-carboxylic acid (Pic) or a 3-amino or 3-hydroxy derivative thereof, anthranilic acid, pyridine-3-carboxylic acid (Nic), pyrazine-2-carboxylic acid, pyrrole-2-carboxylic acid, proline (Pro) or pipecolic acid;

each $R^b$ independently represents serine (Ser), glutamic acid (Glu), aspartic acid (Asp), threonine (Thr) or allothreonine (aThr);

each $R^c$ independently represents aspartic acid (Asp) or glutamic acid (Glu);

each $R^d$ independently represents glycine (Gly) or alanine (Ala);

each $R^e$ independently represents Lysine (Lys), ornithine (Orn) or arginine (Arg);

each Y independently represents a hydroxy or amino group; and n represents 0 or 1, the amino acid residues being present in either the D or the L form.

2. Peptide compounds as claimed in claim 1, wherein:
each $R^a$ independently represents pGlu, Pic or Pro;
each $R^b$ independently represents Ser, Glu or Asp;
each Y independently represents a hydroxy or amino group; and
n represents 0.

3. Peptide compounds as claimed in claim 1, wherein A represents a carbon-carbon bond, a $C_{1-6}$-alkylene group, cis or trans $-CH_2-CH=CH-CH_2-$, $-CH_2-C\equiv C-CH_2-$, $-(CH_2)_p-Z-(CH_2)_q$ wherein Z is O, S or $S_2$ and p and q independently represent 1 or 2, or $-(CH_2)_r-C_6H_4-(CH_2)_s$ wherein r and s independently represent 0 or 1.

4. Peptide compounds as claimed in claim 1, wherein $R^1$ and $R^2$ independently represent hydrogen atoms or methyl groups.

5. Peptide compounds as claimed in claim 1 of formula:

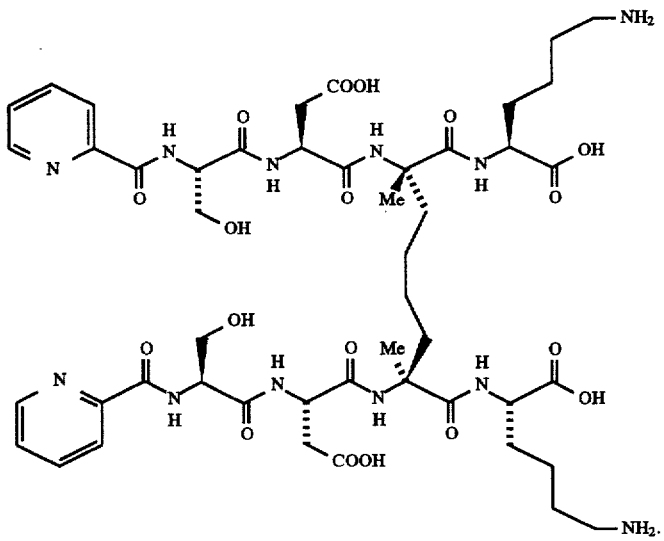

6. A composition containing a peptide compound as claimed in claim 1 and a myelopoiesis inhibitor as a combined preparation for simultaneous, separate or sequential use in cytostatic therapy.

7. A pharmaceutical composition comprising a peptide compound as claimed in claim 1 together with a pharmaceutical carrier or excipient.

8. A method for the stimulation of myelopoiesis or regeneration of bone marrow which comprises administering to a patient in need thereof an effective amount of the composition as claimed in claim 7.

9. A process for producing a peptide compound as claimed in claim 1, said process comprising:

(a) hydrolysing a compound of the formula

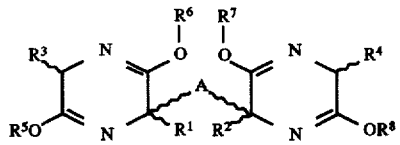

(wherein
A, $R^1$ and $R^2$ are as defined in any one of claims 1 to 5;
$R^3$ and $R^4$ are either the same as $R^1$ and $R^2$ respectively or are alkyl groups; and
$R^5$, $R^6$, $R^7$ and $R^8$ independently represent $C_{1-6}$ alkyl groups or $C_{1-8}$ aralkyl groups) to form a diamino diacid derivative of the formula

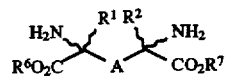

(b) reacting said diamino diacid derivative with successive amino acid derivatives to build up a protected derivative of the bridged peptide of formula I and (c) deprotecting any protected groups present.

* * * * *